(12) United States Patent
Maack

(10) Patent No.: US 7,642,537 B2
(45) Date of Patent: Jan. 5, 2010

(54) RADIOGRAPHY SYSTEM WITH STORAGE MEANS FOR IMAGE CASSETTES

(75) Inventor: Hanns Ingo Maack, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 144 days.

(21) Appl. No.: 11/910,632

(22) PCT Filed: Apr. 4, 2006

(86) PCT No.: PCT/IB2006/051015

§ 371 (c)(1),
(2), (4) Date: Oct. 4, 2007

(87) PCT Pub. No.: WO2006/106477

PCT Pub. Date: Oct. 12, 2006

(65) Prior Publication Data

US 2008/0317214 A1    Dec. 25, 2008

(30) Foreign Application Priority Data

Apr. 8, 2005   (EP) .................................. 05102782

(51) Int. Cl.
*G03B 42/08* (2006.01)
(52) U.S. Cl. .................. 250/584; 250/580; 250/370.09
(58) Field of Classification Search ............ 250/370.09, 250/484.4, 580, 584; 378/182
See application file for complete search history.

(56) References Cited

U.S. PATENT DOCUMENTS

| | | | |
|---|---|---|---|
| 4,893,011 A | 1/1990 | Bauer et al. | |
| 4,908,514 A | 3/1990 | Bauer et al. | |
| 4,960,994 A * | 10/1990 | Muller et al. | 250/584 |
| 5,154,409 A * | 10/1992 | Kondoh | 271/178 |
| 5,218,186 A * | 6/1993 | Kondoh | 235/375 |
| 5,264,684 A * | 11/1993 | Weil | 235/375 |
| 5,334,851 A | 8/1994 | Good et al. | |
| 5,376,806 A * | 12/1994 | Hejazi | 250/584 |
| 5,757,021 A | 5/1998 | Dewaele | |
| 5,865,745 A | 2/1999 | Schmitt et al. | |
| 6,137,861 A * | 10/2000 | Reina et al. | 378/174 |
| 6,346,714 B1 * | 2/2002 | Mueller et al. | 250/589 |
| 6,533,453 B1 | 3/2003 | Heidsieck et al. | |

FOREIGN PATENT DOCUMENTS

| | | |
|---|---|---|
| EP | 0609500 A1 | 8/1994 |
| EP | 1039338 A2 | 9/2000 |
| WO | 2004044815 | 5/2004 |

* cited by examiner

*Primary Examiner*—David P. Porta
*Assistant Examiner*—Mark R Gaworecki

(57) ABSTRACT

The invention relates to a radiography system for computed radiography, comprising an X-ray apparatus (1) with an X-ray source (7), a plurality of image cassettes (9) for producing digital images, a cassette reading means (13) for reading radiographic images (19) stored in the image cassettes (9) after X-ray exposure, and a data processing means (14) connected to the cassette reading means (13), the data processing means (14) being arranged to process the radiographic images (19) read from the image cassettes (9). In order to provide such a radiography system, whereby patient data (18) can be associated with an X-ray image (19) in an easy and reliable manner, the invention proposes to make provision for a cassette storage means (10) associated with the X-ray apparatus (1) for storing the image cassettes (9), wherein the storage means is provided with an identification means (12) connected to the data processing means (14), the identification means being arranged to identify the image cassettes (9) stored in the cassette storage means (10).

18 Claims, 1 Drawing Sheet

RADIOGRAPHY SYSTEM WITH STORAGE MEANS FOR IMAGE CASSETTES

Figure 1:
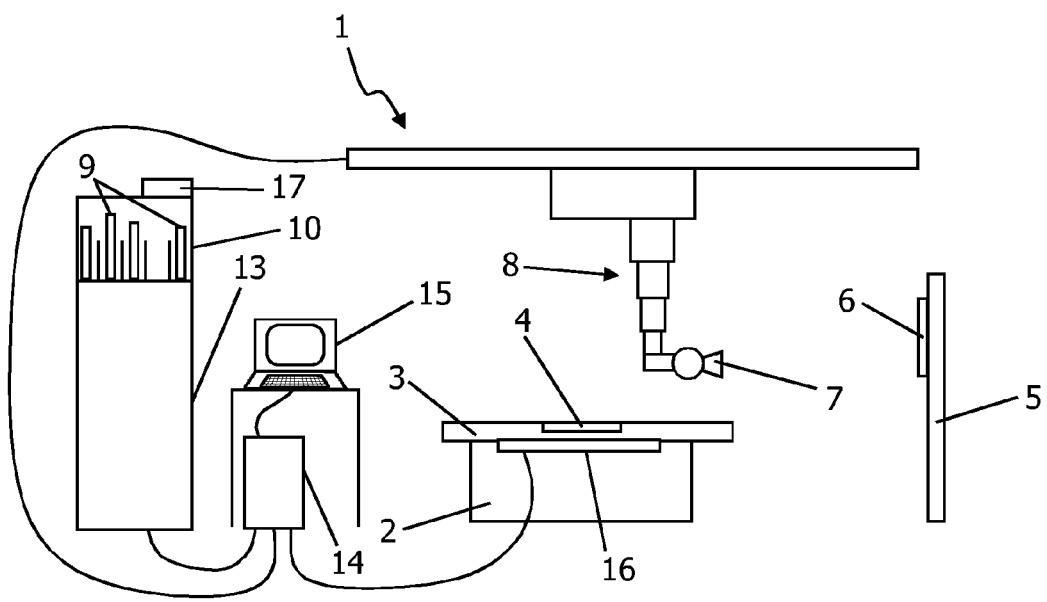

The invention relates to a radiography system for computed radiography, comprising an X-ray apparatus with an X-ray source, a plurality of image cassettes for producing digital images, a cassette reading means for reading radiographic images stored in the image cassettes after X-ray exposure, and a data processing means connected to the cassette reading means, wherein the data processing means is arranged to process the radiographic images read from the image cassettes. Furthermore the invention relates to a computer program for such a radiography system.

In the field of medical diagnostic imaging, and particularly in the field of X-ray radiography, a wide spectrum of equipment is nowadays commercially available. In a conventional X-ray system, the patient is supported during an examination on a radiographic-fluoroscopic table comprising an X-ray image detecting means, e.g. a normal X-ray film, an electronic X-ray image intensifier, or a digital X-ray flat detector. In known computed radiography (CR) systems the radiographic table comprises a housing for an image cassette (so-called CR cassette) containing photostimulable phosphors. An acquired X-ray image is stored on such a CR cassette. An overhead X-ray source, e.g. a conventional X-ray tube, directs a beam of radiation through the patient to the CR cassette underneath the patient. After X-ray exposure the CR image cassette is removed from the X-ray apparatus and inserted into a cassette reader connected to a computer workstation of the X-ray system. The cassette reader reads the stored image and generates digitized image data, which is then processed by the computer workstation and reproduced in the form of an X-ray image on a monitor or display. Usually the cassette reader and the computer workstation are many-room-devices, which means that a single cassette reader is used in combination with a single workstation for the processing of X-ray images acquired by two or more X-ray devices in two or more separate examination rooms. Sometimes the radiographic tables of the known radiography systems also comprise integrated flat panel X-ray detectors that are directly connected to the computer workstation. Depending on the specific requirements of the X-ray examination to be done, this integrated digital X-ray detector can be selected for image acquisition instead of using a CR image cassette.

In a radiography environment of the afore-described kind it is of crucial importance that given patient data (patient name, age, date of examination, etc.) as well as the examination data (parameters of the X-ray exposure, settings of the X-ray apparatus, applied dose, etc.) can be unambiguously associated with a CR image cassette or the X-ray image stored thereon. For this purpose U.S. Pat. No. 5,865,745 teaches to use a dedicated input device with a bar code scanner. The patient data and the examination data is entered by the operator of the radiography system into the device, and a bar code label attached to the CR cassette, which is used for the respective examination, is scanned. This data is stored in the device and then transmitted to the computer workstation of the radiography system in order to be associated with the digital X-ray image.

This known method has the drawback that the workflow for operating the radiography system and the dedicated input device including the handling of the CR image cassettes is complicated and error-prone. The possibility of mixing up the CR cassettes when scanning the bar codes can not be eliminated. Mistakes may be made when the patient data and the examination data are manually entered into the input device. Additional difficulties arise when the known method has to be applied in a radiography environment in which both CR image cassettes and integrated digital image detectors may be selectively used. In this case the operator has to manually enter the information regarding the used X-ray detection means, which further complicates the workflow and enhances the risk of mistakes.

Therefore it is readily appreciated that there is a need for an improved radiography system in order to facilitate the association of patient and examination data with the acquired X-ray images and to facilitate the workflow for the operator of the system. It is consequently the main objective of the invention to provide a radiography system of the kind set forth, whereby the patient and examination data can be associated with an X-ray image in a substantially easier and more reliable manner, while the workflow for operating the system and for handling the image cassettes is significantly simplified.

In accordance with the present invention, a radiography system of the type mentioned above is disclosed, wherein provision is made for a cassette storage means associated with the X-ray apparatus for storing the image cassettes. The storage means is provided with an identification means connected to the data processing means, which identification means is arranged to identify the image cassettes stored in the cassette storage means.

The gist of the invention is to associate a storage space for the CR image cassettes with each X-ray apparatus. In this way the automated control of the use of the image cassettes with the respective X-ray apparatus is enabled. The storage means is equipped with an identification means which detects and identifies the image cassettes in the storage means.

The system according to the invention operates as follows: The image cassettes that are not in use during an examination are in the storage means, where they are detected and identified by the identification means. The data processing means, i.e. the computer workstation of the radiography system, is connected to the identification means and can thus automatically determine, for example by accessing a corresponding data base, which cassette from a given set of CR image cassettes associated with the X-ray apparatus is not in the storage means. This must necessarily be the cassette being in use for the respective X-ray image acquisition. The identification means of the storage means can alternatively be arranged to generate directly a cassette-in-use signal indicating which cassette from the given set of cassettes associated with the X-ray apparatus is not in the cassette storage means during an X-ray exposure. In any case the information determining the identity of the cassette being in use during an X-ray exposure can advantageously be utilized to automatically associate the X-ray image read from this cassette after exposure with a patient data set and/or an examination data set. An unambiguous and error-free association of the image with the corresponding patient is guaranteed in this way.

Furthermore the workflow for image acquisition is simplified significantly by the system of the invention: At first the operator of the system enters the patient data and the type of X-ray examination to be carried out into the workstation. In a hospital environment for example it would also be possible to select the data of the patient to be examined directly from a corresponding patient data base accessed by the workstation. Thereafter the operator enters the examination room and takes a CR cassette from the storage means as required. He has not to take care at all about the association of the image stored in the cassette after X-ray exposure with the data of the examined patient. When the operator inserts the cassette after exposure into the reader, the image data is read and automatically associated with the correct patient data. As a last step the operator has to reinsert the cassette into the storage means such that the system is ready for the next patient.

As mentioned above, the X-ray apparatus of the radiography system may be equipped with an integrated digital X-ray image detector connected directly to the data processing means. In this case it is advantageous if the system is arranged to activate the integrated digital X-ray image detector automatically if the identification means indicates that all cassettes are in the cassette storage means. In this way the operator has not to select manually between the different operation modes 'CR cassette' or 'integrated detector' of the X-ray apparatus. If no cassette is taken from the storage means it is automatically concluded that the integrated detector is to be used. Furthermore the data processing means can advantageously be arranged to associate an image acquired with the integrated detector automatically with the corresponding patient and examination data.

In accordance with a preferred embodiment of the invention, the data processing means (the computer workstation) of the radiography system may be arranged to automatically control the X-ray apparatus depending on the attributes of the cassette in use. For example the individual dimensions of the available cassettes may be stored in the memory of the workstation. The collimation of the X-ray source may then be adjusted accordingly under control of the workstation.

It is advantageous if the radiography system of the invention is arranged to inhibit X-ray exposure if the identification means indicates that more than one cassette from the given set of CR cassettes is not in the cassette storage means. If more than one cassette is not in the storage means, it can not be unambiguously concluded which cassette is presently in use, and the system is unable to associate patient and examination data with an acquired X-ray image. By inhibiting X-ray exposure it is made sure that no image can be acquired at all in such a situation. The system automatically enters a 'not ready' state if more than one cassette is not in the storage means.

In accordance with a further preferred embodiment of the invention provision is made for a status display for displaying a status message depending on the cassette-in-use signal generated by the identification means or by the data processing means.

In accordance with the invention it is advantageous if the cassette reading means is integral with the cassette storage means. The cassette storage means with the integrated reading means may comprise a plurality of slots for the CR image cassettes. This makes the workflow for operation of the system still more simple. The cassette has only to be reinserted into the integrated reading and storage means after X-ray exposure. It is not necessary to use a separate cassette reader for reading the X-ray image stored in the cassette before it is reinserted into the storage means.

The identification means of the cassette storage means can be arranged in accordance with the invention to register cassette identifiers attached to each CR image cassette. These identifiers may be printed machine-readable code labels (e.g. bar code labels) or digital transponders. The identification means may thus comprise bar code readers associated with the individual storage spaces for the CR image cassettes or a transponder reader capable of communicating with passive transponder devices attached to the CR cassettes in the storage means.

For the operation of the radiography system according to the invention a computer program may be loaded into the memory of the workstation of the system, which program comprises instructions for checking the presence of image cassettes in the cassette storage means and for identifying a cassette from the given set of image cassettes, which is not in the storage means, as the cassette in use during an X-ray exposure. The automated identification of the cassette in use during an X-ray exposure is the central functional feature of the radiography system of the invention. It is particularly advantageous if the program comprises further instructions for associating the processed radiographic image with a patient data set and/or an examination data set. Such a computer program may be made available for the users of a radiography system on a suitable data carrier like a CD-ROM or a diskette, or it may be downloaded into the memory of the workstation from an internet server.

Figure 2:
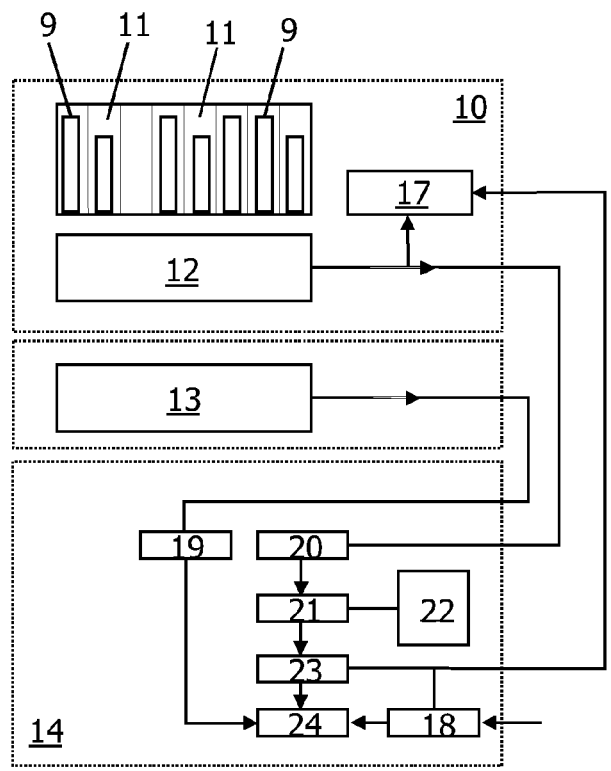

The following drawings disclose preferred embodiments of the present invention. It should be understood, however, that the drawings are designed for the purpose of illustration only and not as a definition of the limits of the invention. In the drawings FIG. 1 illustrates a radiography system according to the invention;

FIG. 2 shows schematically the operation of the storage means of the system depicted in FIG. 1.

With reference to FIG. 1 and FIG. 2, a radiography system in accordance with the present invention is described. An X-ray apparatus 1 of the system comprises a table 2 with a table top 3 for supporting a patient during an examination. The table 2 has a receptacle 4 for a computed radiography (CR) image cassette. Furthermore, provision is made for a wall stand 5 also comprising a receptacle 6 for an image cassette. This wall stand 5 can be used for examination of a patient in a standing position. An overhead X-ray source 7 directs a beam of radiation through the patient to the image cassette underneath or behind the patient. The X-ray source 7 is mounted on a ceiling support system 8 to support the X-ray source 7 and to enable vertical and horizontal movement of the X-ray source 7. A set of differently shaped CR image cassettes 9 containing photostimulable phosphors is inserted into corresponding slots 11 of a cassette storage space 10. A cassette identification means 12 is integral part of the storage space 10. The cassette identification means 12 comprises an RFID (radio frequency identification) reader (not depicted) for reading transponder code labels attached to the image cassettes 9 inserted into the slots 11. The identification means 12 is arranged to detect whether a cassette 9 is in a slot 11 and to register the identity of the respective cassette 9 by reading its transponder label. The storage space 10 further comprises a display 17 for displaying a status message depending on the identification of cassettes 9 in the slots 11. Provision is made for a cassette reader 13 for reading radiographic images stored in the image cassettes 9. The reader 13, which is also integral with the storage space 10, scans an exposed cassette 9 while it is in one of the slots 11 in order to convert the image stored in the photostimulable phosphor of the cassette 9 into a digital image. Further provision is made for a data processing means 14, namely a computer workstation of the radiography system. The workstation 14 is connected to a user terminal 15 comprising a monitor and a keyboard. The digital image data 19 read from the image cassettes 9 is processed by the workstation 14 and displayed on the monitor of the terminal 15. The workstation 14 is connected to the X-ray apparatus 1 for controlling the operation of the X-ray source 7. Furthermore the table 2 of the X-ray apparatus 1 comprises an integrated digital X-ray detector (X-ray flat detector) 16 connected directly to the workstation 14. The detector 16 may be used for image acquisition instead of using one of the CR image cassettes 9.

The workflow of X-ray image acquisition with the system depicted in FIG. 1 and FIG. 2 may be as follows:

At first the operator of the system enters patient data (patient name, date of birth, date of examination) 18 into the terminal 15 of the workstation 14.

Then the operator selects a cassette 9 for the examination to be done and takes it from the storage space 10.

The identification means 12 identifies the cassettes 9 remaining in the slots 11 of the storage space 10. On this basis the workstation 14 determines which cassette from the given set of available cassettes 9 is missing (see next step). This cassette is identified as the cassette in use. Correspondingly, the message 'cassette XY in use for patient AB' is displayed on the status display 17 (XY is the number of the respective cassette, while AB is the name of the patient to be examined).

A cassette identification data set 20 identifying the cassettes 9 in the storage space 10 is transferred to the workstation 14. In a step 21 the cassette identification data set 20 is matched with a data base 22 which contains identification data of the set of available cassettes 9. From this match cassette-in-use data 23 identifying the cassette 9 selected by the operator for image acquisition is generated.

The workstation 14 now automatically controls the X-ray apparatus. Since a cassette has been taken from the storage space 10 it is concluded that this cassette is to be used for image acquisition. Consequently the integrated digital image detector 16 is deactivated. Furthermore, the collimator of the X-ray source 7 is set in accordance with the dimensions of the selected cassette 9.

The operator places the cassette 9 in the receptacle 4 of the table 2, and initiates the X-ray exposure.

The status display 17 now changes to the message 'reinsert cassette XY into the storage slot'. In this state the system is not ready in order to avoid double X-ray exposure of cassette 9. The operator takes the cassette 9 from the receptacle 4 to the storage space 10, where it is identified by the identification means 12 and read out by the integrated reader 13. The message on the status display 17 changes to 'readout of cassette XY in progress'.

The X-ray image data 19 is transferred to the workstation 14 where it is further processed and displayed on the terminal 15.

In step 24 the image data 14 read from the selected cassette 9 is automatically associated with the patient data 18.

The radiography system of the invention further enables automated quality control. The given set of cassettes 9 is associated with the X-ray apparatus 9 such that the use of the cassettes can be monitored. The workstation 14 counts the number of exposures for each cassette and can display this information via the terminal 15. Depending on the number of exposures an automated request to perform a quality test with a frequently used cassette or to replace an old cassette by a new one can be generated.

Furthermore the system mode can be automatically selected depending on the number of cassettes 9 detected in the storage space 10 by identification means 12:

If all cassettes 9 are in the storage space 10 the integrated digital image detector 16 of the X-ray apparatus 1 is automatically activated and used for image acquisition.

If it is detected that one of the cassettes from the given set of available cassettes 9 is not in the storage space 10, the missing cassette is automatically determined as cassette in use and the integrated detector 16 is disabled.

If the identification means 12 detects that more than one cassette of the set of cassettes 9 is not in the storage space 10, the system is not ready and the message 'reinsert cassette in storage slot' appears on the status display 17.

As stated above, it is an important aspect of the invention that a given set of cassettes 9, which are to be stored in the storage space 10, is associated with the X-ray apparatus 1. In a multi-room environment (not depicted) this means that a separate set of cassettes 9 is assigned to each examination room. In this case it is comfortable for the operator of the system to have the cassettes 9 in the storage space 10 together with the reader 13 accommodated in the respective examination room. The storage space 10 has to be provided with an X-ray shielding (e.g. lead shielding) to avoid that scattered radiation pre-exposes the cassettes 9 that are not in use. As described above, the system will avoid X-ray exposure automatically if it is detected by the identification means 12 that more than one cassette 9 is not in the storage space 10.

The invention claimed is:

1. A radiography system for computed radiography, comprising:

an X-ray apparatus with an X-ray source;

a plurality of image cassettes for producing digital images;

a cassette reading means for reading radiographic images stored in the image cassettes after X-ray exposure;

a data processing means connected to the cassette reading means, the data processing means being arranged to process the radiographic images read from the image cassettes;

an integrated digital X-ray image detector connected directly to the data processing means;

a cassette storage means associated with the X-ray apparatus for storing the image cassettes, wherein the storage means is provided with an identification means connected to the data processing means, the identification means being arranged to identify the image cassettes stored in the cassette storage means;

wherein the data processing means or the identification means are arranged to generate a cassette-in-use signal indicating which cassette from the plurality of image cassettes is not in the cassette storage means during an X-ray exposure, and the data processing means is arranged to activate the integrated digital X-ray image detector automatically if the cassette-in-use signal indicates that all cassettes from the plurality of image cassettes are in the cassette storage means.

2. Radiography system according to claim 1, wherein the data processing means is arranged to process the cassette-in-use signal and to automatically associate an image read from an image cassette after X-ray exposure with a patient data set or an examination data set, which patient data set comprises data identifying the examined patient, and which examination data set comprises data relating to the parameters of the X-ray apparatus during exposure.

3. Radiography system according to claim 1, wherein the data processing means is arranged to associate an image detected by the integrated digital X-ray image detector with a patient data set and/or an examination data set.

4. Radiography system according to claim 1, wherein provision is made for a status display for displaying a status message depending on the cassette-in-use signal.

5. Radiography system according to claim 1, wherein the cassette reading means is integral with the cassette storage means, which cassette storage means comprises a plurality of slots for the image cassettes.

6. Radiography system according to claim 1, wherein the identification means is arranged to register cassette identifiers attached to each image cassette, the identifiers being printed code labels or digital transponders.

7. Radiography system according to claim 1, wherein the system comprises two or more X-ray apparatuses, each being accommodated in a separate examination room together with a plurality of image cassettes and a cassette storage means for storing the image cassettes associated with the respective X-ray apparatus.

8. A radiography system for computed radiography, comprising:
  an X-ray apparatus with an X-ray source;
  a plurality of image cassettes for producing digital images;
  a cassette reading means for reading radiographic images stored in the image cassettes after X-ray exposure;
  a data processing means connected to the cassette reading means, the data processing means being arranged to process the radiographic images read from the image cassettes;
  an integrated digital X-ray image detector connected directly to the data processing means;
  a cassette storage means associated with the X-ray apparatus for storing the image cassettes, wherein the storage means is provided with an identification means connected to the data processing means, the identification means being arranged to identify the image cassettes stored in the cassette storage means;
  wherein the data processing means or the identification means are arranged to generate a cassette-in-use signal indicating which cassette from the plurality of image cassettes is not in the cassette storage means during an X-ray exposure;
  wherein the data processing means is connected to the X-ray apparatus and arranged to control the X-ray apparatus depending on the cassette-in-use signal; and
  wherein the data processing means is arranged to inhibit X-ray exposure if the cassette-in-use signal indicates that more than one cassette from the plurality of image cassettes is not in the cassette storage means.

9. A computer-readable data carrier comprising computer program instructions for automatically activating a radiography system for computed radiography, the method comprising:
  providing a radiography system for computed radiography comprising:
    an X-ray apparatus with an X-ray source;
    a plurality of image cassettes for producing digital images;
    a cassette reading means for reading radiographic images stored in the image cassettes after X-ray exposure;
    a data processing means connected to the cassette reading means, the data processing means being arranged to process the radiographic images read from the image cassettes;
    an integrated digital X-ray image detector connected directly to the data processing means;
    a cassette storage means associated with the X-ray apparatus for storing the image cassettes, wherein the storage means is provided with an identification means connected to the data processing means, the identification means being arranged to identify the image cassettes stored in the cassette storage means;
  generating a cassette-in-use signal with the data processing means or the identification means indicating which cassette from the plurality of image cassettes is not in the cassette storage means during an X-ray exposure, and
  activating the integrated digital X-ray image detector automatically if the cassette-in- use signal indicates that all cassettes from the plurality of image cassettes are in the cassette storage means.

10. A computer-readable data carrier comprising computer program instructions for automatically inhibiting a radiography system for computed radiography, the method comprising:
  providing a radiography system for computed radiography comprising:
    an X-ray apparatus with an X-ray source;
    a plurality of image cassettes for producing digital images;
    a cassette reading means for reading radiographic images stored in the image cassettes after X-ray exposure;
    a data processing means connected to the cassette reading means, the data processing means being arranged to process the radiographic images read from the image cassettes;
    an integrated digital X-ray image detector connected directly to the data processing means;
    a cassette storage means associated with the X-ray apparatus for storing the image cassettes, wherein the storage means is provided with an identification means connected to the data processing means, the identification means being arranged to identify the image cassettes stored in the cassette storage means;
  generating a cassette-in-use signal with the data processing means or the identification means indicating which cassette from the plurality of image cassettes is not in the cassette storage means during an X-ray exposure, wherein the data processing means is connected to the X-ray apparatus and arranged to control the X-ray apparatus depending on the cassette-in-use signal; and
  inhibiting X-ray exposure if the cassette-in-use signal indicates that more than one cassette from the plurality of image cassettes is not in the cassette storage means.

11. A method for automatically activating a radiography system for computed radiography, the method comprising:
  providing a radiography system for computed radiography comprising:
    an X-ray apparatus with an X-ray source;
    a plurality of image cassettes for producing digital images;
    a cassette reading means for reading radiographic images stored in the image cassettes after X-ray exposure;
    a data processing means connected to the cassette reading means, the data processing means being arranged to process the radiographic images read from the image cassettes;
    an integrated digital X-ray image detector connected directly to the data processing means;
    a cassette storage means associated with the X-ray apparatus for storing the image cassettes, wherein the storage means is provided with an identification means connected to the data processing means, the identification means being arranged to identify the image cassettes stored in the cassette storage means;
  generating a cassette-in-use signal with the data processing means or the identification means indicating which cassette from the plurality of image cassettes is not in the cassette storage means during an X-ray exposure, and activating the integrated digital X-ray image detector automatically if the cassette-in- use signal indicates that all cassettes from the plurality of image cassettes are in the cassette storage means.

12. The method of claim 11, further comprising prescribing exposure parameters for the X-ray apparatus in accordance with the attributes of the cassette in use.

13. The method of claim 12, further comprising:
reading a radiographic image stored in the cassette in use after an X-ray exposure;
processing the radiographic image read from the cassette in use.

14. The method of claim 13, further comprising associating the processed radiographic image with a patient data set or an examination data set, the patient data set comprising data identifying the examined patient, and the examination data set comprising the exposure parameters of the X-ray apparatus.

15. A method for automatically inhibiting a radiography system for computed radiography, the method comprising:
providing a radiography system for computed radiography comprising:
an X-ray apparatus with an X-ray source;
a plurality of image cassettes for producing digital images;
a cassette reading means for reading radiographic images stored in the image cassettes after X-ray exposure;
a data processing means connected to the cassette reading means, the data processing means being arranged to process the radiographic images read from the image cassettes;
an integrated digital X-ray image detector connected directly to the data processing means;
a cassette storage means associated with the X-ray apparatus for storing the image cassettes, wherein the storage means is provided with an identification means connected to the data processing means, the identification means being arranged to identify the image cassettes stored in the cassette storage means;
generating a cassette-in-use signal with the data processing means or the identification means indicating which cassette from the plurality of image cassettes is not in the cassette storage means during an X-ray exposure, wherein the data processing means is connected to the X-ray apparatus and arranged to control the X-ray apparatus depending on the cassette-in-use signal; and
inhibiting X-ray exposure if the cassette-in-use signal indicates that more than one cassette from the plurality of image cassettes is not in the cassette storage means.

16. The method of claim 15, further comprising prescribing exposure parameters for the X-ray apparatus in accordance with the attributes of the cassette in use.

17. The method of claim 16, further comprising:
reading a radiographic image stored in the cassette in use after an X-ray exposure;
processing the radiographic image read from the cassette in use.

18. The method of claim 17, further comprising associating the processed radiographic image with a patient data set or an examination data set, the patient data set comprising data identifying the examined patient, and the examination data set comprising the exposure parameters of the X-ray apparatus.

* * * * *